United States Patent
Fluehmann et al.

(10) Patent No.: US 6,784,207 B2
(45) Date of Patent: Aug. 31, 2004

(54) PHYTANIC ACID DERIVATIVE COMPOSITIONS

(75) Inventors: Beat Fluehmann, Zurich (CH); Willi Hunziker, Magden (CH)

(73) Assignee: Roche Vitamins Inc., Parsippany, NJ (US)

(*) Notice: Subject to any disclaimer, the term of this patent is extended or adjusted under 35 U.S.C. 154(b) by 224 days.

(21) Appl. No.: 09/915,152

(22) Filed: Jul. 25, 2001

(65) Prior Publication Data

US 2002/0082298 A1 Jun. 27, 2002

(30) Foreign Application Priority Data

Aug. 4, 2000 (EP) .............................................. 00116848

(51) Int. Cl.⁷ .............................................. A61K 31/20
(52) U.S. Cl. ...................................... 514/560; 514/866
(58) Field of Search ................................. 514/560, 866

(56) References Cited

FOREIGN PATENT DOCUMENTS

| DE | 196 44 422 A1 | 10/1996 |
| WO | WO 97/09039 | 3/1997 |

OTHER PUBLICATIONS

Derwent English language abstract of JP 52 085125 (1977).
Derwent English language abstract of DE 196 44 422 (Document B2 above).

Lemotte et al., "Phytanic acid is a retinoid X receptor ligand," *Eur. J. Biochem.*, vol. 236, No. 1, pp. 328–333 (1996).

McCarty, M.F., "The chlorophyll metabolite phytanic acid is a natural rexinoid—potential for treatment and prevention of diabetes," *Medical Hypotheses*, vol. 56, No. 2, pp. 217–219 (2001).

Mukherjee et al., "Sensitization of diabetic and obese mice to insulin by retinoid X receptor agonists," *Nature*, vol. 386, No. 6623, pp. 407–410 (1997).

Van Den Branden et al., "Phytol and Peroxisome Proliferation," *Pediatric Research*, vol. 20, No. 5, pp. 411–415 (1986).

*Primary Examiner*—Kevin E. Weddington
(74) *Attorney, Agent, or Firm*—Bryan Cave LLP

(57) ABSTRACT

The present invention is a method for the treatment or prevention of preferably non-insulin dependent (NIDDM or so-called Type II) diabetes mellitus, or other conditions associated with impaired glucose tolerance such as obesity, and in particular to the use of phytanic acid derivatives for the said treatment and/or prevention. A method of making a composition for the treatment or prevention of non-insulin dependent diabetes mellitus and related diseases comprising combining phytanic acid or derivatives thereof with a pharmaceutically acceptable additive or adjuvant, and a composition for the treatment or prevention of non-insulin dependent diabetes mellitus comprising phytanic acid or derivatives thereof are also provided.

6 Claims, 7 Drawing Sheets

SEQUENCE LISTING

<160> NUMBER OF SEQ ID NOS: 45

<210> SEQ ID NO 1
<211> LENGTH: 23
<212> TYPE: DNA
<213> ORGANISM: Artificial
<220> FEATURE:
<223> OTHER INFORMATION: Synthetic oligonucleotide used for the amplification of GLUT-1.

<400> SEQUENCE: 1
ggttcatcat cagcatggag ttc                                           23

<210> SEQ ID NO 2
<211> LENGTH: 21
<212> TYPE: DNA
<213> ORGANISM: Artificial
<220> FEATURE:
<223> OTHER INFORMATION: Synthetic oligonucleotide used for the amplification of GLUT-1.

<400> SEQUENCE: 2
gggcatgatt ggttccttct c                                             21

<210> SEQ ID NO 3
<211> LENGTH: 27
<212> TYPE: DNA
<213> ORGANISM: Artificial
<220> FEATURE:
<223> OTHER INFORMATION: Synthetic oligonucleotide used for the amplification of GLUT-1.

<400> SEQUENCE: 3
cctgccaaag cgattaacaa agaggcc                                       27

<210> SEQ ID NO 4
<211> LENGTH: 20
<212> TYPE: DNA
<213> ORGANISM: Artificial
<220> FEATURE:
<223> OTHER INFORMATION: Synthetic oligonucleotide used for the amplification of GLUT-2.

<400> SEQUENCE: 4
cgccctctgc ttccagtaca                                               20

<210> SEQ ID NO 5
<211> LENGTH: 19
<212> TYPE: DNA
<213> ORGANISM: Artificial
<220> FEATURE:
<223> OTHER INFORMATION: Synthetic oligonucleotide used for the amplification of GLUT-2.

<400> SEQUENCE: 5
aggaccaccc cagcaaaaa                                                19

<210> SEQ ID NO 6
<211> LENGTH: 24
<212> TYPE: DNA
<213> ORGANISM: Artificial
<220> FEATURE:
<223> OTHER INFORMATION: Synthetic oligonucleotide used for the amplification of GLUT-2.

<400> SEQUENCE: 6
cggacttcct cgggccttac gtgt                                          24

<210> SEQ ID NO 7
<211> LENGTH: 19
<212> TYPE: DNA
<213> ORGANISM: Artificial
<220> FEATURE:
<223> OTHER INFORMATION: Synthetic oligonucleotide used for the
     amplification of glucokinase.

<400> SEQUENCE: 7
cgtggatggc tccgtgtac                                                19

<210> SEQ ID NO 8
<211> LENGTH: 18
<212> TYPE: DNA
<213> ORGANISM: Artificial
<220> FEATURE:
<223> OTHER INFORMATION: Synthetic oligonucleotide used for the
     amplification of glucokinase.

<400> SEQUENCE: 8
tgtcagcctg cgcacact                                                 18

<210> SEQ ID NO 9
<211> LENGTH: 24
<212> TYPE: DNA
<213> ORGANISM: Artificial
<220> FEATURE:
<223> OTHER INFORMATION: Synthetic oligonucleotide used for the
     amplification of glucokinase.

<400> SEQUENCE: 9
agctgcaccc gagcttcaag gagc                                          24

<210> SEQ ID NO 10
<211> LENGTH: 21
<212> TYPE: DNA
<213> ORGANISM: Artificial
<220> FEATURE:
<223> OTHER INFORMATION: Synthetic oligonucleotide used for the
     amplification of PEPCK.

<400> SEQUENCE: 10
cgctggatgt cagaagagga c                                             21

<210> SEQ ID NO 11
<211> LENGTH: 19
<212> TYPE: DNA
<213> ORGANISM: Artificial
<220> FEATURE:
<223> OTHER INFORMATION: Synthetic oligonucleotide used for the
     amplification of PEPCK.

<400> SEQUENCE: 11
acatggtgcg gcctttcat                                                19

<210> SEQ ID NO 12
<211> LENGTH: 24
<212> TYPE: DNA
<213> ORGANISM: Artificial
<220> FEATURE:
<223> OTHER INFORMATION: Synthetic oligonucleotide used for the
     amplification of PEPCK.

<400> SEQUENCE: 12
aaagcattca acgccaggtt cccg                                          24

<210> SEQ ID NO 13
<211> LENGTH: 21
<212> TYPE: DNA
<213> ORGANISM: Artificial
<220> FEATURE:
<223> OTHER INFORMATION: Synthetic oligonucleotide used for the
      amplification of ApoA1.

<400> SEQUENCE: 13
gccactgtgt atgtggatgc a                                             21

<210> SEQ ID NO 14
<211> LENGTH: 20
<212> TYPE: DNA
<213> ORGANISM: Artificial
<220> FEATURE:
<223> OTHER INFORMATION: Synthetic oligonucleotide used for the
      amplification of ApoA1.

<400> SEQUENCE: 14
ttgcccaaag tggaggattc                                               20

<210> SEQ ID NO 15
<211> LENGTH: 29
<212> TYPE: DNA
<213> ORGANISM: Artificial
<220> FEATURE:
<223> OTHER INFORMATION: Synthetic oligonucleotide used for the
      amplification of ApoA1.

<400> SEQUENCE: 15
acagcggcag agactatgtg tcccagttt                                     29

<210> SEQ ID NO 16
<211> LENGTH: 20
<212> TYPE: DNA
<213> ORGANISM: Artificial
<220> FEATURE:
<223> OTHER INFORMATION: Synthetic oligonucleotide used for the
      amplification of ApoE.

<400> SEQUENCE: 16
ggtccaggaa gagctgcaga                                               20

<210> SEQ ID NO 17
<211> LENGTH: 22
<212> TYPE: DNA
<213> ORGANISM: Artificial
<220> FEATURE:
<223> OTHER INFORMATION: Synthetic oligonucleotide used for the
      amplification of ApoE.

<400> SEQUENCE: 17
ccgtcatagt gtcctccatc ag                                            22

<210> SEQ ID NO 18
<211> LENGTH: 27
<212> TYPE: DNA
<213> ORGANISM: Artificial
<220> FEATURE:
<223> OTHER INFORMATION: Synthetic oligonucleotide used for the
      amplification of ApoE.

<400> SEQUENCE: 18
ctcccaagtc acacaggaac tgacggt                                       27

```
<210> SEQ ID NO 19
<211> LENGTH: 30
<212> TYPE: DNA
<213> ORGANISM: Artificial
<220> FEATURE:
<223> OTHER INFORMATION: Synthetic oligonucleotide used for the
      amplification of Cyp7a.

<400> SEQUENCE: 19
gactggaaaa aatttcatta cactacttct                                      30

<210> SEQ ID NO 20
<211> LENGTH: 22
<212> TYPE: DNA
<213> ORGANISM: Artificial
<220> FEATURE:
<223> OTHER INFORMATION: Synthetic oligonucleotide used for the
      amplification of Cyp7a.

<400> SEQUENCE: 20
cgtggtattt ccatcatttg gg                                              22

<210> SEQ ID NO 21
<211> LENGTH: 27
<212> TYPE: DNA
<213> ORGANISM: Artificial
<220> FEATURE:
<223> OTHER INFORMATION: Synthetic oligonucleotide used for the
      amplification of Cyp7a.

<400> SEQUENCE: 21
cgaaggcatt tggacacaga agcattg                                         27

<210> SEQ ID NO 22
<211> LENGTH: 20
<212> TYPE: DNA
<213> ORGANISM: Artificial
<220> FEATURE:
<223> OTHER INFORMATION: Synthetic oligonucleotide used for the
      amplification of Cyp4a1.

<400> SEQUENCE: 22
gcagttccca tcacctccct                                                 20

<210> SEQ ID NO 23
<211> LENGTH: 25
<212> TYPE: DNA
<213> ORGANISM: Artificial
<220> FEATURE:
<223> OTHER INFORMATION: Synthetic oligonucleotide used for the
      amplification of Cyp4a1.

<400> SEQUENCE: 23
tgctgtagtt ctttgtcacc ttgaa                                           25

<210> SEQ ID NO 24
<211> LENGTH: 24
<212> TYPE: DNA
<213> ORGANISM: Artificial
<220> FEATURE:
<223> OTHER INFORMATION: Synthetic oligonucleotide used for the
      amplification of Cyp4a1.

<400> SEQUENCE: 24
ccactggttc tttgggcaca agca                                            24
```

```
<210> SEQ ID NO 25
<211> LENGTH: 20
<212> TYPE: DNA
<213> ORGANISM: Artificial
<220> FEATURE:
<223> OTHER INFORMATION: Synthetic oligonucleotide used for the
      amplification of HMG-CoA reductase.

<400> SEQUENCE: 25
tggctggtga gttgtccttg                                                 20

<210> SEQ ID NO 26
<211> LENGTH: 26
<212> TYPE: DNA
<213> ORGANISM: Artificial
<220> FEATURE:
<223> OTHER INFORMATION: Synthetic oligonucleotide used for the
      amplification of HMG-CoA reductase.

<400> SEQUENCE: 26
ttatctttga tctgttgtga accatg                                          26

<210> SEQ ID NO 27
<211> LENGTH: 23
<212> TYPE: DNA
<213> ORGANISM: Artificial
<220> FEATURE:
<223> OTHER INFORMATION: Synthetic oligonucleotide used for the
      amplification of HMG-CoA reductase.

<400> SEQUENCE: 27
atgtcctgct gccaatgctg cca                                             23

<210> SEQ ID NO 28
<211> LENGTH: 17
<212> TYPE: DNA
<213> ORGANISM: Artificial
<220> FEATURE:
<223> OTHER INFORMATION: Synthetic oligonucleotide used for the
      amplification of LCAT.

<400> SEQUENCE: 28
catgcggatc ctggcct                                                    17

<210> SEQ ID NO 29
<211> LENGTH: 25
<212> TYPE: DNA
<213> ORGANISM: Artificial
<220> FEATURE:
<223> OTHER INFORMATION: Synthetic oligonucleotide used for the
      amplification of LCAT.

<400> SEQUENCE: 29
tctctcagct ttatgttgga catga                                           25

<210> SEQ ID NO 30
<211> LENGTH: 22
<212> TYPE: DNA
<213> ORGANISM: Artificial
<220> FEATURE:
<223> OTHER INFORMATION: Synthetic oligonucleotide used for the
      amplification of LCAT.

<400> SEQUENCE: 30
aggtgacaac cagggcatcc cg                                              22
```

-continued

<210> SEQ ID NO 31
<211> LENGTH: 17
<212> TYPE: DNA
<213> ORGANISM: Artificial
<220> FEATURE:
<223> OTHER INFORMATION: Synthetic oligonucleotide used for the
      amplification of LDLR.

<400> SEQUENCE: 31
ggtggtcagc agcccct                                                    17

<210> SEQ ID NO 32
<211> LENGTH: 21
<212> TYPE: DNA
<213> ORGANISM: Artificial
<220> FEATURE:
<223> OTHER INFORMATION: Synthetic oligonucleotide used for the
      amplification of LDLR.

<400> SEQUENCE: 32
cagctgcgat ggatacactc a                                               21

<210> SEQ ID NO 33
<211> LENGTH: 27
<212> TYPE: DNA
<213> ORGANISM: Artificial
<220> FEATURE:
<223> OTHER INFORMATION: Synthetic oligonucleotide used for the
      amplification of LDLR.

<400> SEQUENCE: 33
cctccctcga gttccactgt ggcagta                                         27

<210> SEQ ID NO 34
<211> LENGTH: 23
<212> TYPE: DNA
<213> ORGANISM: Artificial
<220> FEATURE:
<223> OTHER INFORMATION: Synthetic oligonucleotide used for the
      amplification of LFABP.

<400> SEQUENCE: 34
caaggtgatc cacaatgagt tca                                             23

<210> SEQ ID NO 35
<211> LENGTH: 21
<212> TYPE: DNA
<213> ORGANISM: Artificial
<220> FEATURE:
<223> OTHER INFORMATION: Synthetic oligonucleotide used for the
      amplification of LFABP.

<400> SEQUENCE: 35
gaccttttcc ccagtcatgg t                                               21

<210> SEQ ID NO 36
<211> LENGTH: 24
<212> TYPE: DNA
<213> ORGANISM: Artificial
<220> FEATURE:
<223> OTHER INFORMATION: Synthetic oligonucleotide used for the
      amplification of LFABP.

<400> SEQUENCE: 36
tgggggagga gtgcgaactg gaga                                            24

<210> SEQ ID NO 37

<210> SEQ ID NO 37
<211> LENGTH: 16
<212> TYPE: DNA
<213> ORGANISM: Artificial
<220> FEATURE:
<223> OTHER INFORMATION: Synthetic oligonucleotide used for the
      amplification of LPL.

<400> SEQUENCE: 37
tcgggcccag caactt                                                        16

<210> SEQ ID NO 38
<211> LENGTH: 19
<212> TYPE: DNA
<213> ORGANISM: Artificial
<220> FEATURE:
<223> OTHER INFORMATION: Synthetic oligonucleotide used for the
      amplification of LPL.

<400> SEQUENCE: 38
ggccacatca tttcccacc                                                     19

<210> SEQ ID NO 39
<211> LENGTH: 26
<212> TYPE: DNA
<213> ORGANISM: Artificial
<220> FEATURE:
<223> OTHER INFORMATION: Synthetic oligonucleotide used for the
      amplification of LPL.

<400> SEQUENCE: 39
tccagtgtct gccggctata ccaagc                                             26

<210> SEQ ID NO 40
<211> LENGTH: 21
<212> TYPE: DNA
<213> ORGANISM: Artificial
<220> FEATURE:
<223> OTHER INFORMATION: Synthetic oligonucleotide used for the
      amplification of TNFalpha.

<400> SEQUENCE: 40
tcgtaggtca aaccaccaag c                                                  21

<210> SEQ ID NO 41
<211> LENGTH: 18
<212> TYPE: DNA
<213> ORGANISM: Artificial
<220> FEATURE:
<223> OTHER INFORMATION: Synthetic oligonucleotide used for the
      amplification of TNFalpha.

<400> SEQUENCE: 41
tattggccag gagggcgt                                                      18

<210> SEQ ID NO 42
<211> LENGTH: 26
<212> TYPE: DNA
<213> ORGANISM: Artificial
<220> FEATURE:
<223> OTHER INFORMATION: Synthetic oligonucleotide used for the
      amplification of TNFalpha.

<400> SEQUENCE: 42
aggagcagct ggagtggctg agccag                                             26

<210> SEQ ID NO 43
<211> LENGTH: 24

```
-continued

<212> TYPE: DNA
<213> ORGANISM: Artificial
<220> FEATURE:
<223> OTHER INFORMATION: Synthetic oligonucleotide used for the
      amplification of Beta-actin.

<400> SEQUENCE: 43
gacaggatgc agaggagatt actg                                          24

<210> SEQ ID NO 44
<211> LENGTH: 23
<212> TYPE: DNA
<213> ORGANISM: Artificial
<220> FEATURE:
<223> OTHER INFORMATION: Synthetic oligonucleotide used for the
      amplification of Beta-actin.

<400> SEQUENCE: 44
ccaccgatcc acacagagta ctt                                           23

<210> SEQ ID NO 45
<211> LENGTH: 26
<212> TYPE: DNA
<213> ORGANISM: Artificial
<220> FEATURE:
<223> OTHER INFORMATION: Synthetic oligonucleotide used for the
      amplification of Beta-actin.

<400> SEQUENCE: 45
tcaagatcat tgctcctcct gagcgc                                        26
```

PHYTANIC ACID DERIVATIVE COMPOSITIONS

FIELD OF THE INVENTION

The present invention relates to phytanic acid derivatives and their use for the treatment or the prevention of diabetes mellitus.

BACKGROUND OF THE INVENTION

This invention relates to a novel method for the treatment or prevention of preferably non-insulin dependent (NIDDM or so-called Type II) diabetes mellitus, and in particular to the use of phytanic acid derivatives for the treatment or prevention of NIDDM.

NIDDM is the form of diabetes mellitus that occurs predominantly in adults in whom adequate production of insulin is available for use, yet a defect exists in insulin-mediated utilization and metabolism of glucose in peripheral tissues. Overt NIDDM is characterized by three major metabolic abnormalities: elevated serum glucose levels, resistance to insulin-mediated glucose disposal, and overproduction of glucose by the liver.

Previous mechanisms of action of oral antidiabetics such as the generally used sulfonyl ureas are primarily based on an increased release of insulin from the beta cells of the pancreas, a mechanism which in the long term may lead to accelerated exhaustion of the endogenous production of insulin in diabetics. The modern view of the pathobiochemistry of adult-onset diabetes mellitus therefore emphasizes the need to treat the peripheral insulin resistance that is present in this case.

The human diet contains phytol, a metabolite of the chlorophyll molecule. Phytol is metabolized to phytenic acid and phytanic acid (see FIG. 6). Intestinal absorption of phytol from dietary chlorophyll was shown to be minimal (Baxter, J. H. & Steinberg, D. (1967) Absorption of phytol from dietary chlorophyll in the rat, J Lipid Res. 8, 615–20; Baxter, J. H. (1968) Absorption of chlorophyll phytol in normal man and in patients with Refsum's disease, J Lipid Res. 9, 636–41).

In rats, phytol is much less well adsorbed than phytanic acid (Baxter, J. H., Steinberg, D., Mize, C. E. & Avigan, J. (1967) Absorption and metabolism of uniformly $^{14}$C-labeled phytol and phytanic acid by the intestine of the rat studied with thoracic duct cannulation, Biochim Biophys Acta. 137, 277–90).

In humans, dairy products and ruminant fats in the human diet are the major sources of phytanic acid. A normal diet contains 50–100 mg of phytanic acid per day (Steinberg. (1995) Refsum Disease in the Metabolic and Molecular Bases of Inherited Metabolic Disorders pp. 2351–2369, McGraw-Hill, New York). Phytenic- and phytanic acid levels in normal human serum were 2 $\mu$M and 6 $\mu$M (Avigan, J. (1966) The presence of phytanic acid in normal human and animal plasma, Biochim Biophys Acta. 116, 391–4). Phytanic acid may be elevated 50-fold in patients with heredopathia atactica polyneuritiformis (Refsum's disease), an inherited metabolic disorder characterized by an α-hydroxylase gene defect that prevents the conversion of phytanic acid to pristanic acid (Verhoeven, N. M., Wanders, R. J., Poll-The, B. T., Saudubray, J. M. & Jakobs, C. (1998) The metabolism of phytanic acid and pristanic acid in man: a review, J Inherit Metab Dis. 21, 697–728).

In adult mice fed a 0.5% phytol diet for 21 days a 40% decrease in the triglyceride serum levels was noted. However, cholesterol serum levels remained unaffected (Van den Branden, C., Vamecq, J., Wybo, I. & Roels, F. (1986) Phytol and peroxisome proliferation, Pediatr Res. 20, 411–5). Moreover, expression of enzymes, known to be involved in beta-oxidation and regulated by peroxisome proliferator-activated receptor (PPAR) was observed to be up regulated. Recently it was shown that phytanic acid is a 9-cis-retinoic acid receptor (RXR) as well as a PPARα ligand (Kitareewan, S., Burka, L. T., Tomer, K. B., Parker, C. E., Deterding, L. J., Stevens, R. D., Forman, B. M., Mais, D. E., Heyman, R. A., McMorris, T. & Weinberger, C. (1996) Phytol metabolites are circulating dietary factors that activate the nuclear receptor RXR, Molecular Biology of the Cell. 7, 1153–66.; Lemotte, P. K., Keidel, S. & Apfel, C. M. (1996) Phytanic acid is a retinoid X receptor ligand, Eur J Biochem. 236, 328–33; Wolfrum, C., Ellinghaus, P., Fobker, M., Seedorf, U., Assmann, G., Borchers, T. & Spener, F. (1999) Phytanic acid is ligand and transcriptional activator of murine liver fatty acid binding protein, J Lipid Res. 40, 708–14.; Ellinghaus, P., Wolfrum, C., Assmann, G., Spener, F. & Seedorf, U. (1999) Phytanic acid activates the peroxisome proliferator-activated receptor alpha (PPARalpha) in sterol carrier protein 2-/sterol carrier protein x-deficient mice, J Biol Chem. 274, 2766–72 and WO 97/09039).

RXR receptor binding and transcriptional effects were observed with EC50 and IC50 of 3 $\mu$M and 2.3 $\mu$M respectively. The Kd-value for phytanic acid as PPARα ligand is reported as 10 nM (Ellinghaus et al., supra). In contrast to the ability of 9-cis-retinoic acid to activate both RXR and all-trans-retinoic acid receptor (RAR) (EC50 2.5 nM and 13 nM), phytanic acid activity is restricted to RXR receptors. Activation of both PPARα and RXR by phytanic acid and the specificity with respect to the retinoid receptors may lead to a distinct pattern of gene induction as opposed to the pattern observed in other fatty acids.

Liver is second to skeletal muscle as the most important tissue in glucose metabolism and therefore is an important regulator of glucose level in plasma. It is well known that activation of PPARγ by the antidiabetic thiazolidinediones such as troglitazone rosiglitazone and pioglitazone leads to restored insulin sensitivity in case of diabetes mellitus type II (Berger, J., Bailey, P., Biswas, C., Cullinan, C. A., Doebber, T. W., Hayes, N. S., Saperstein, R., Smith, R. G. & Leibowitz, M. D. (1996) Thiazolidinediones produce a conformational change in peroxisomal proliferator-activated receptor-gamma: binding and activation correlate with antidiabetic actions in db/db mice, Endocrinology. 137, 4189–95; Lehmann, J. M., Moore, L. B., Smith-Oliver, T. A., Wilkison, W. O., Willson, T. M. & Kliewer, S. A. (1995) An antidiabetic thiazolidinedione is a high affinity ligand for peroxisome proliferator-activated receptor gamma (PPARγ), J Biol Chem. 270, 12953–6.12, 13). Expression of PPARα as well as PPARγ was shown in liver of rodents and humans (Mukherjee, R., Jow, L., Croston, G. E. & Paterniti, J. R., Jr. (1997) Identification, characterization, and tissue distribution of human peroxisome proliferator-activated receptor (PPAR) isoforms PPARγ2 versus PPARγ1 and activation with retinoid X receptor agonists and antagonists, J Biol Chem. 272, 8071–6.; Lemberger, T., Braissant, O., Juge-Aubry, C., Keller, H., Saladin, R., Staels, B., Auwerx, J., Burger, A. G., Meier, C. A. & Wahli, W. (1996) PPAR tissue distribution and interactions with other hormone-signaling pathways, Ann N Y Acad Sci. 804, 231–51; Palmer, C. N., Hsu, M. H., Griffin, K. J., Raucy, J. L. & Johnson, E. F. (1998) Peroxisome proliferator activated receptor-alpha expression in human liver, Mol Pharmacol. 53, 14–22. ; Vidal-Puig, A. J., Considine, R. V., Jimenez-Linan, M., Werman, A., Pories, W. J., Caro, J. F. & Flier, J. S. (1997) Peroxisome proliferator-activated receptor gene expression in human tissues. Effects of obesity, weight loss, and regulation by insulin and glucocorticoids, J Clin Invest. 99, 2416–22).

Phytanic acid was described as a ligand for both RXR and PPARα (Kitareewan, et al. (supra); Lemotte et al. (supra); Ellinghaus et al (supra) and WO97/09039). Decaux et al. (Decaux, J. F., Juanes, M., Bossard, P. & Girard, J. (1997) Effects of triiodothyronine and retinoic acid on glucokinase gene expression in neonatal rat hepatocytes, Mol Cell Endocrinol. 130, 61–7) demonstrated in primary cultures of rat hepatocytes, an up-regulation of glucokinase mRNA by retinoic acid. Together with the finding that the phosphoenolpyruvate carboxykinase (PEPCK) gene is regulated among other responsive elements by a PPAR responsive element (PPRE) (Juge-Aubry, C., Pernin, A., Favez, T., Burger, A. G., Wahli, W., Meier, C. A. & Desvergne, B. (1997) DNA binding properties of peroxisome proliferator-activated receptor subtypes on various natural peroxisome proliferator response elements. Importance of the 5'-flanking region, J Biol Chem. 272, 25252–9; Hanson, R. W. & Reshef, L. (1997) Regulation of phosphoenolpyruvate carboxykinase (GTP) gene expression, Annu Rev Biochem. 66, 581–611), a RXR/PPAR mediated up-regulation of the glucose influx in hepatocytes could be a reasonable explanation. PPAR forms permissive heterodimers with RXR, meaning that either partner can regulate the transcriptional activity by interacting with its own ligand. Co-treatment of the cells with ligands for PPAR as well as RXR results in an additive effect. Moreover it was shown that ligands selective for RXR could activate PPRE driven reporter genes (Kliewer, S. A., Umesono, K., Noonan, D. J., Heyman, R. A. & Evans, R. M. (1992) Convergence of 9-cis retinoic acid and peroxisome proliferator signaling pathways through heterodimer formation of their receptors, Nature. 358, 771–4; Gearing, K. L., Gottlicher, M., Teboul, M., Widmark, E. & Gustafsson, J. A. (1993) Interaction of the peroxisome-proliferator-activated receptor and retinoid X receptor, Proc Natl Acad Sci U S A. 90, 1440–4; Keller, H., Dreyer, C., Medin, J., Mahfoudi, A., Ozato, K. & Wahli, W. (1993) Fatty acids and retinoids control lipid metabolism through activation of peroxisome proliferator-activated receptor-retinoid X receptor heterodimers, Proc Natl Acad Sci U S A. 90, 2160–4).

In vivo sensitization to insulin was observed in diabetic and obese mice in response to RXR agonists, comparable to the effects known from the thiazolidinediones (Mukherjee, R., Davies, P. J., Crombie, D. L., Bischoff, E. D., Cesario, R. M., Jow, L., Hamann, L. G., Boehm, M. F., Mondon, C. E., Nadzan, A. M., Paterniti, J. R., Jr. & Heyman, R. A. (1997) Sensitization of diabetic and obese mice to insulin by retinoid X receptor agonists, Nature. 386, 407–10).

However, there is no indication in the prior art that phytanic acid derivatives, preferably phytanic acid, would have a beneficial effect on NIDDM itself.

SUMMARY OF THE INVENTION

Surprisingly, experiments showed that phytanic acid derivatives, preferably phytanic acid, can increase and stimulate the transcription of the genes for glucose transporters and glucokinase resulting in increased glucose uptake in hepatocytes.

Moreover, phytanic acid derivatives normalize and increase the glucose level without a concomitant risk of hypoglycemia and is thus excellently suited for the treatment or prevention of diabetes mellitus.

An object of the present invention is therefore a novel method for the treatment or prevention of preferably NIDDM.

This object is achieved by the use of phytanic acid derivatives for the treatment or prevention of diabetes mellitus, preferably diabetes mellitus type II per se. In a particular embodiment the use of phytanic acid is preferred.

One embodiment of the present invention is a method of making a composition for the treatment or prevention of a disease selected from the group consisting of non-insulin dependent diabetes mellitus, syndrome X, hyperlipidaemia, hypertension, hyperinsulinaemia, hypercholesterinaemia, hypertriglycerinaemia, impaired glucose tolerance and related obesity comprising combining phytanic acid or a phytanic acid derivative with a pharmaceutically acceptable carrier.

Another embodiment of the present invention is a composition for the treatment or prevention of non-insulin dependent diabetes mellitus comprising phytanic acid or a derivative thereof.

A further embodiment of the invention is a dietary supplement comprising a composition comprising phytanic acid or a derivative thereof.

Another embodiment of the invention is a method of treating or preventing non-insulin dependent diabetes mellitus comprising administering to a human or an animal an effective dose of a pharmaceutical composition or a dietary supplement comprising phytanic acid, a phytanic acid precursor, or a derivative phytanic acid.

Another embodiment of the invention is a method for increasing cellular glucose uptake comprising administering to an animal or a human in need of increased cellular glucose uptake a phytanic acid derivative or a phytanic acid precursor in an effective amount to increase cellular glucose uptake.

Another embodiment of the invention is a method of reducing plasma insulin comprising administering to a mammal a plasma insulin reducing amount of a composition comprising phytanic acid or a derivative thereof.

Abbreviations

In the present invention, the following abbreviations are used: Apolipoprotein A1 (ApoA1) and Apolipoprotein E (ApoE), cytochrome P450/4A1 (Cyp4a1), cholesterol 7α-hydroxylase and glucokinase (Cyp7a), docohexaenoic acid (DHA), facilitative glucose transporter (GLUT), 3-hydroxy-3-methylglutaryl-CoA (HMG-CoA)-reductase, lipoprotein lipase (LPL), low-density lipoprotein receptor (LDLR), liver fatty acid binding protein (LFABP), phosphoenolpyruvate carboxykinase (PEPCK), peroxisome proliferator-activated receptor (PPAR), PPAR responsive element (PPRE), all-trans-retinoic acid receptor (RAR), 9-cis-retinoic acid receptor (RXR), tumor necrosis factor α (TNFα).

DETAILED DESCRIPTION OF THE INVENTION

One embodiment of the present invention is a method of making a composition for the treatment or prevention of non-insulin dependent diabetes mellitus and related diseases by combining phytanic acid or derivatives thereof with a pharmaceutically acceptable additive or adjuvant.

Figure 3:
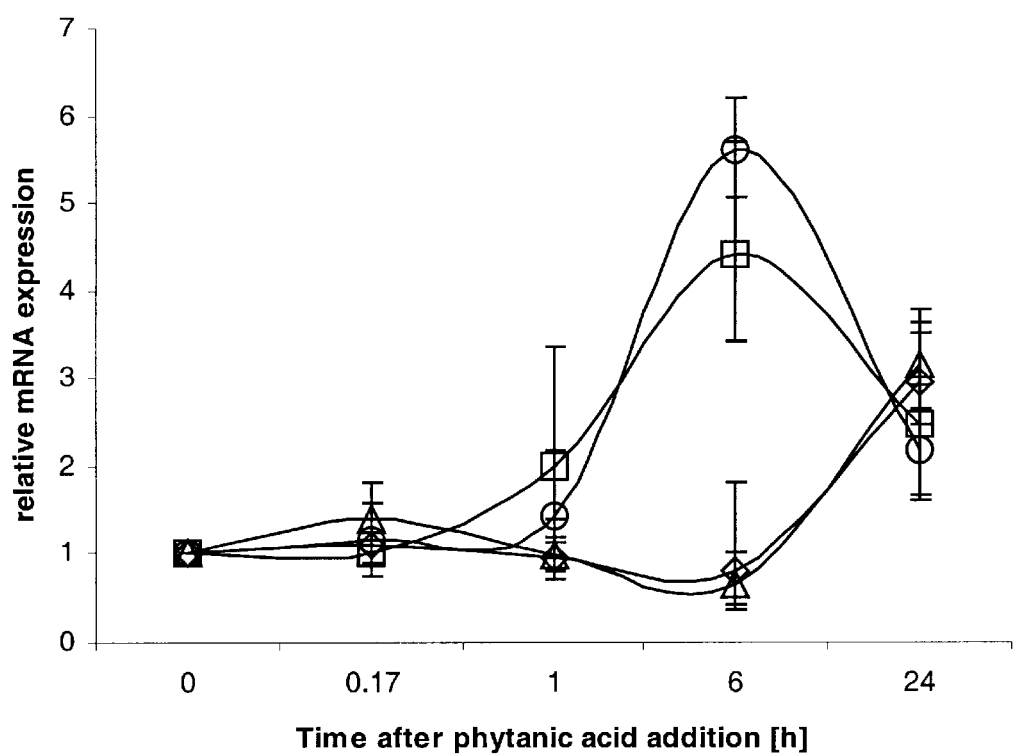
FIG. 3 shows mRNA levels for GLUT-1 (○), GLUT-2 (◇), glucokinase (Δ), and PEPCK (□) were determined with the TaqMan™ at different time points after stimulation of the rat primary hepatocytes with 100 µM phytanic acid. mRNA levels were normalized to β-actin expression and expressed relative to untreated cells. The data is presented as means of 3 independent experiments. Error bars were calculated as described in Example 3.

As used herein "treatment or prevention of non-insulin dependent diabetes mellitus and related diseases" means the administration of an effective amount of phytanic acid, a precursor of phytanic acid or a derivative of phytanic acid to a mammal to elicit a measurable physiological effect in the mammal, such as for example, increased expression of GLUT-1, or GLUT-2 as set forth in Example 3 (FIGS. 3 and 4 ) or a reduction in plasma insulin levels as set forth in Example 4.

In the present invention, the rat model is used. Thus, the in vivo and in vitro benefits of the presently claimed compositions are shown with rats fed a diet of the presently claimed compositions, as well as rat hepatocytes exposed to such compositions. It is well recognized that for non-insulin dependent diabetes mellitus and related diseases as defined herein that the rat is a good model for other mammalian species including humans. Thus, as used herein, "mammal" includes rats, swine, bovine, equine, and human.

Another embodiment of the present invention is a composition for the treatment or prevention of non-insulin dependent diabetes mellitus containing phytanic acid or derivatives thereof.

A further embodiment of the present invention is a method of treating or preventing non-insulin dependent diabetes mellitus having the following steps:
  a) making a pharmaceutical composition or a dietary supplement comprising a phytanic acid, a phytanic acid derivative, a phytanic acid precursor, or combinations thereof; and
  b) administering the pharmaceutical composition or dietary supplement to a human.

The present invention demonstrates that glucose uptake in primary cultures of hepatocytes is markedly induced by levels of phytanic acid derivatives one order of magnitude higher than serum concentration. The enzymes involved in glucose uptake are the various members of the facilitative glucose transporter (GLUT) family, GLUT-1, GLUT-2, and GLUT-4 (see (Olson, A. L. & Pessin, J. E. (1996) Structure, function, and regulation of the mammalian facilitative glucose transporter gene family, Annu Rev Nutr. 16, 235–56)) and glucokinase. The up regulation of the mRNA levels of GLUT-1 and GLUT-2 observed in the present invention are accompanied by an increased 2-deoxy-D-glucose uptake. The liver type glucose transporter GLUT-2 is distinguished from the other GLUT isoforms by being a low-affinity glucose transporter with a high turnover rate (Gould, G. W., Thomas, H. M., Jess, T. J. & Bell, G. I. (1991) Expression of human glucose transporters in Xenopus oocytes: kinetic characterization and substrate specificities of the erythrocyte, liver, and brain isoforms, Biochemistry. 30, 5139–45).

The presence of a low affinity glucose transporter ensures that in liver, glucose flux is directly proportional to the plasma glucose concentration. Moreover, in hepatocytes GLUT-2 is coupled with the regulated phosphorylating activity provided by the glucokinase. Thus, during states of glycogen synthesis, glucokinase is up regulated and can increase the formation of intracellular glucose-6-phosphate, maintaining a low intracellular concentration of free glucose (Magnuson, M. A., Andreone, T. L., Printz, R. L., Koch, S. & Granner, D. K. (1989) Rat glucokinase gene: structure and regulation by insulin, Proc Natl Acad Sci U S A. 86, 4838–42).

Therefore, a further object of the present invention relates to phytanic acid derivatives which are able to serve as a modulator, having the activity to induce or to stimulate the gene expression of the above mentioned enzymes, and to provide an enhanced serum glucose clearance by improved liver glucose uptake.

Figure 6:
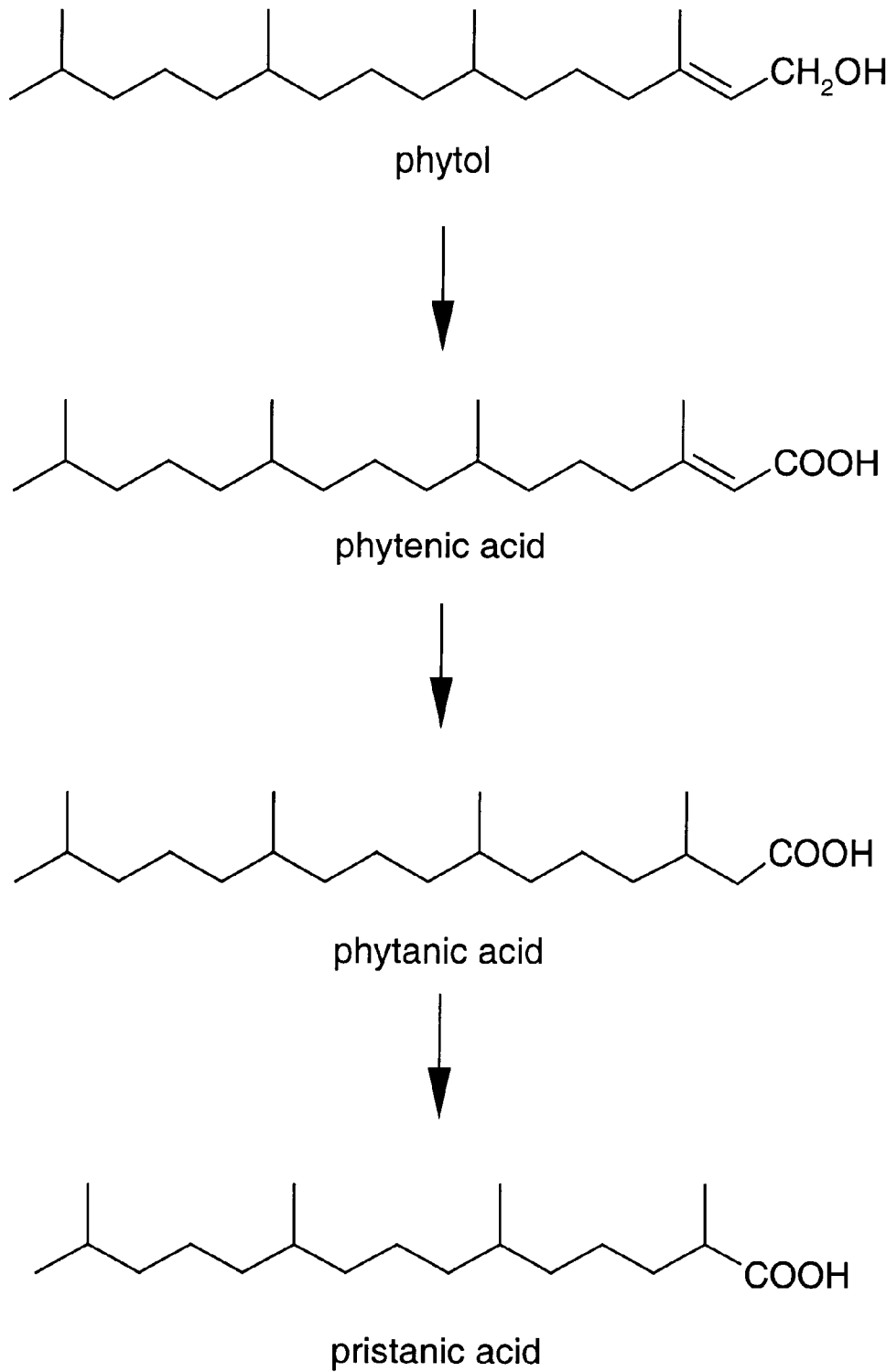
FIG. 6 shows precursors and metabolites of phytanic acid. Metabolism proceeds from phytol to phytanic acid through phytenic acid.

As used herein the term "phytanic acid derivatives" includes phytanic acid as such or its precursors (as depicted in FIG. 6), wherein phytenic acid and phytol are preferred. Furthermore, derivatives thereof such as, but not limited to, hydroxy-phytanic acid or hydroxy-phytenic acid, especially 2-hydroxy-phytenic acid or 2-hydroxy-phytenic ester, hydroxy-phytanic esters, phytanic amides, phytenic amides, hydroxy-phytanic amides, hydroxy-phytenic amides, hydrocarbon esters, phospholipid esters and triacylglyceryl esters, with long chain n-alkyl esters, preferably C12–C22, are preferred.

Of course, all the listed acids and derivatives are pharmaceutical acceptable or physiologically applicable derivatives. In addition the present invention also relates to pharmaceutically acceptable compounds derived therefrom. Moreover, the present invention relates to pharmaceutical acceptable salts of the phytanic acid and/or phytenic acid or derivatives thereof, e.g., alkali metal, alkaline-earth metal, ammonium and alkylammonium salts such as a Na, K, Mg, Ca, or tetramethylammonium salt, or pharmaceutically acceptable solvates thereof. Suitable pharmaceutically acceptable salts include acid addition salts. Suitable acid addition salts include pharmaceutically acceptable inorganic salts such as sulfates, nitrates, phosphates, borates, hydrochlorides, and hydrobromides and pharmaceutically acceptable organic acid addition salts such as acetates, tartrate maleates, citrates, succinates, benzoates, ascorbates, methane-sulfonates, alpha keto glutarates, and alpha-glycerophosphate. Suitable pharmaceutically acceptable solvates include hydrates.

As used herein the term "pharmaceutical acceptable" or "physiologically applicable" means compounds, compositions, and ingredients for both human and veterinary (for example swine, bovine, chicken, and turkey) use, administering in an effective pharmaceutical amount in a human or animal.

Diabetics often suffer from a complete derangement of the entire metabolic condition characterized by hyperlipidaemia, increase in cholesterol (hypercholesterinaemia, hypertriglycerinaemia), hypertension, obesity, and hyperinsulinaemia, a clinical entity which is referred to as metabolic syndrome or syndrome X and leads to a very wide range of late complications. Apart from decreasing hyperinsulinaemia, phytanic acid and/or phytenic acid or derivatives thereof also decrease triglycerides, cholesterol, and fibrinogen and are thus excellently suitable for treating the metabolic syndrome. Therefore, phytanic acid and/or phytenic acid or derivatives thereof are also useful for the treatment or prevention of such conditions associated with diabetes mellitus. In this context, the present invention embraces especially the treatment or prevention of the so-called impaired glucose tolerance and related obesity.

In a further embodiment of the present invention phytanic acid derivatives are also useful to accompany or to support an insulin therapy in combination with known active compounds.

In the above mentioned treatments or prevention, the phytanic acid derivatives may be administered per se or, preferably, as a pharmaceutical composition also containing a pharmaceutically acceptable carrier.

Accordingly, the present invention also provides a pharmaceutical composition for the treatment or prevention of Type II diabetes mellitus, which composition contains phytanic acid derivatives and a pharmaceutically acceptable carrier therefor.

The composition may, if desired, be in the form of a pack accompanied by written or printed instructions for use. Usually the pharmaceutical compositions of the present invention will be adapted for oral or parenteral administration, although compositions for administration by other routes, such as by injection and percutaneous absorption are also envisaged. Particularly suitable compositions for oral administration are unit dosage forms such as tablets and capsules. Other fixed unit dosage forms, such as powders presented in sachets, may also be used. In accordance with conventional pharmaceutical practice, the carrier may contain a diluent, filler, disintegrate, wetting agent, lubricant, colorant, flavorant, and/or other conventional adjuvants. Typical carriers include, for example, microcrystalline cellulose, starch, sodium atarch glycollate, polyvinyl pyrrolidone, polyvinylpolypyrrolidone, magnesium stearate, sodium lauryl sulfate, or sucrose.

Most suitably the composition will be formulated in unit dose form. Such unit dose will normally contain an amount of the active ingredient in the range of from about 0.1 to about 1000 mg, more usually about 0.1 to about 500 mg, and more especially about 0.1 to about 100 mg. Conveniently, the active ingredient may be administered as a pharmaceutical composition hereinbefore defined, and this forms a particular aspect of the present invention. In the above mentioned treatments the phytanic acid derivatives, may be taken in doses such as those described above, one to six times a day in a manner such that the total daily dose for a 70 kg adult will generally be in the range of from about 0.1 to about 6000 mg, and more usually about 1 to about 1500 mg, generally about 0.5 to about 10 mg. The daily dose of the active compound is usually about 0.1 to about 50 mg/kg body weight. Usually about 0.5 to about 40 mg/kg/day and preferably about 1.0 to about 20 mg/kg/day are effective in one or several administrations per day in order to obtain the desired results. Of course, the administered dose depends on the age, state of health, and weight of the recipient, the extent of the disease, the type of additional treatments that may be carried out at the same time, and the type of desired effect.

In a preferred embodiment phytanic acid derivatives, preferably phytanic acid as such, is/are administrated to a human or animal, whereby potential target cells, such as liver cells, are exposed to a concentration of about 10 to about 100 $\mu$M of the phytanic acid derivative.

No unacceptable toxicological effects are observed when the active compounds are administered in accordance with the above-mentioned invention.

A further preferred embodiment of the present invention is a dietary supplement, which may also be referred to as a nutraceutical composition for the prevention of non-insulin dependent diabetes mellitus, wherein the composition comprises phytanic acid derivatives as food or feed additives or ingredients and further additives and/or adjuvants.

The following examples are provided to further illustrate the compositions and methods of the present invention. These examples are illustrative only and are not intended to limit the scope of the invention in any way.

EXAMPLES

Materials

Ham F12 cell culture medium and the fatty acid free artificial serum supplement BMS were purchased from Life Technologies Inc., Gaithersburg, Md. and Biochrom KG, Berlin, Germany, respectively. Phytanic acid, palmitic acid, DHA, and neutral red were obtained from Sigma-Aldrich Co, Buchs, Switzerland. PCR-primers were purchased from Life Technologies Inc., Gaithersburg, Md. and TaqMan™-probes from Integrated DNA Technologies, Inc., Coralville Iowa.

Cell Culture

Primary rat hepatocytes were obtained as previously described (Goldlin, C. R. & Boelsterli, U. A. (1991) Reactive oxygen species and non-peroxidative mechanisms of cocaine-induced cytotoxicity in rat hepatocyte cultures, Toxicology. 69, 79–91). Cells were cultured in 6-well plates in a fatty acid free medium (Ham F12 supplemented with 10% BMS) at 37° C. in a humidified atmosphere containing 5% $CO_2$; and stimulated in a time and dose dependent manner with phytanic acid, palmitic acid, or DHA.

Example 1

Cell Viability

Viability of cells cultivated under the above conditions was determined by neutral red uptake assay (Maria C.

Martinez-Diez, Maria A. Serrano, Maria J. Monte, Jose J. G. Manin, Comparison of the effects of bile acids on cell viability and DNA synthesis by rat hepatocytes in primary culture, Biochimica et Biophysica Acta 1500 (2000) 153–160). In brief, a final Neutral red concentration of 50 µg/ml in sterile PBS was used. This solution was prewarmed to 37° C. before its use. The cells were washed once with PBS to remove non-adherent and dead cells. This was replaced by Neutral red-containing medium. The cultures were incubated for 3 h at 37° C. in an atmosphere of 5% $CO_2$, 95% air allowing the lysosomes and Golgi apparatus of viable cells to take up the dye. The cultures were then carefully washed with Neutral red-free PBS to eliminate remaining extracellular dye. The incorporated Neutral red was eluted from the hepatocytes with 50% ethanol supplemented with 1% acetic acid for 10 min. Absorbance at 535 nm of the eluate was measured.

Figure 1:
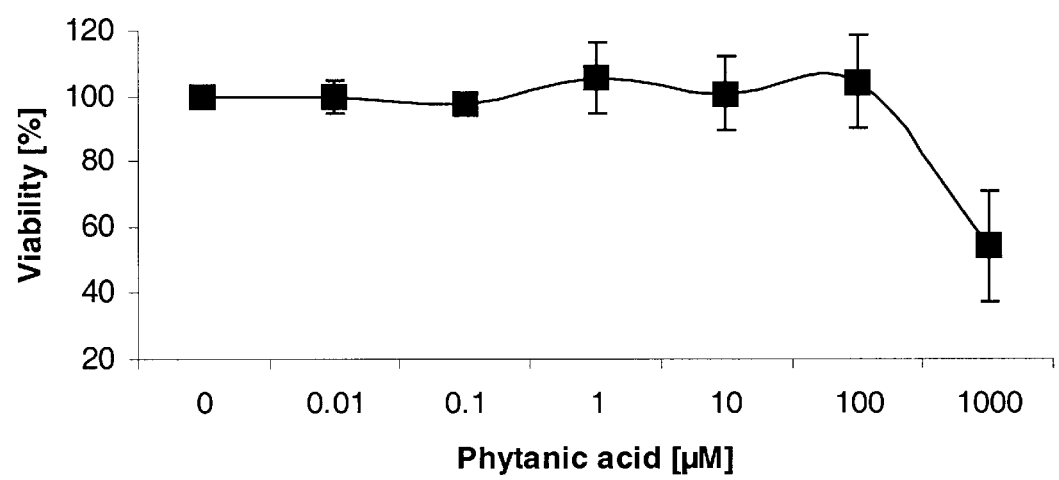
FIG. 1 shows the effect of phytanic acid on cell viability. Rat primary hepatocytes were cultured in media containing various amounts of phytanic acid for 24 h at 37° C. Subsequently cell viability was determined using the neutral red uptake assay. The data is presented as means±SD of 3 independent experiments.

The effect of various phytanic acid concentrations on cell viability was measured with the neutral red uptake assay (FIG. 1). Incubation of the hepatocytes for 24 h with up to 100 µM phytanic acid showed no effect on cell viability. At the concentration of 1 mM phytanic acid only 54±17% of the cells survived compared to untreated.

Example 2

2-deoxy-D-glucose Uptake

Cells cultured in 24-well plates were treated for 24 h with phytanic acid, palmitic acid, and DHA. Subsequently the medium was removed and cells were washed twice with pre-warmed phosphate buffered saline, pH 7.4 (PBS). 500 µl of pre-warmed glucose reaction mixture (0.01 mM 2-deoxy-D-glucose and 3 µCi/ml [3H]-2-deoxy-D-glucose in PBS) was then added to the cells. The reaction mixture was further incubated at 37° C. for different time intervals. The reaction was terminated by aspirating the reaction mixture and washing the cells twice with ice cold 10 mM 2-deoxy-D-glucose in PBS. Cells were then solubilized with 500 µl of 1% sodium dodecyl sulfate, 400 µl of which was transferred to scintillation vials containing 5 ml Quickszint 1 (Zinsser Analytic, Frankfurt, Germany). Radioactivity was counted in a Tri-Carb 2500 (Packard, Meriden, Conn.) liquid scintillation counter. The remaining lysate was used for protein content determination with the BCA Protein Assay Reagent Kit (Pierce, Rockford, Ill.). Data are expressed as means±SD from 3 independent experiments.

Figure 2:
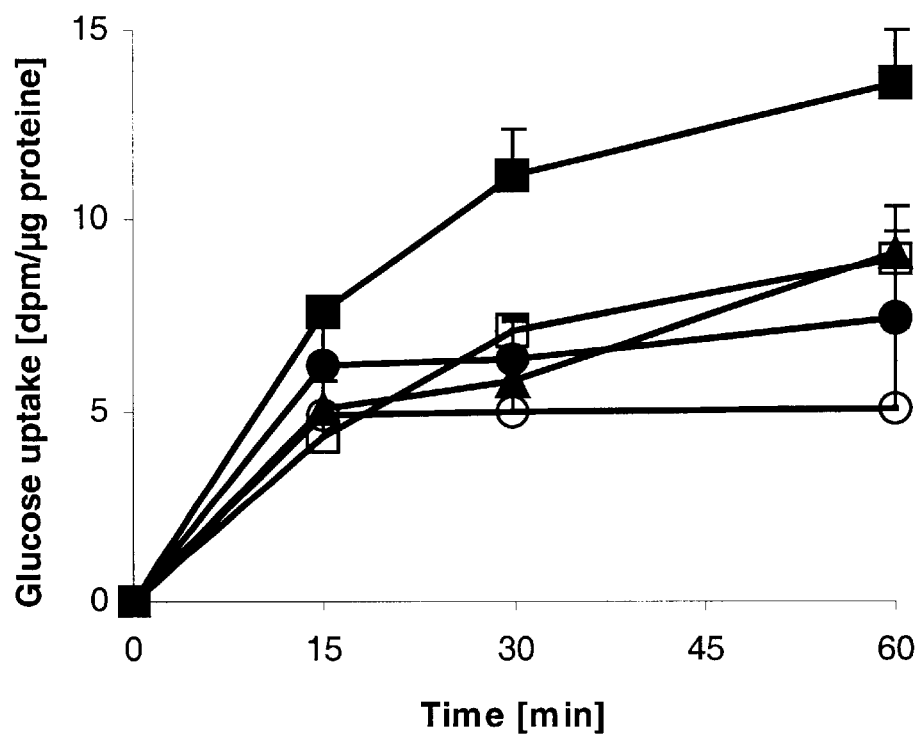
FIG. 2 shows glucose uptake in hepatocytes. Rat primary hepatocytes were cultured for 24 h at 37° C. in media containing phytanic acid 10 μM (□) and 100 μM (▌), palmitic acid 100 µM (●), DHA 100 µM (○), and control (▼). Subsequently [3H]-2-deoxy-D-glucose uptake was measured after 15, 30, and 60 min incubation period. The data is presented as means±SD of 3 independent experiments.

Measurement of 2-deoxy-D-glucose uptake in primary rat hepatocytes cultures during the time course of study, revealed a substantial increase of 2-deoxy-D-glucose uptake in hepatocytes treated with 100 µM phytanic acid as compared with the control, palmitic acid or DHA (FIG. 2). In cells treated with phytanic acid at concentrations lower than 100 µM no measurable effect on 2-deoxy-D-glucose uptake was observed.

Example 3

Quantitative RT-PCR: mRNA Expression in Response to Phytanic Acid

For the quantification of the expression levels the novel Real Time Quantitative TaqMan™ PCR using the multiplex method was employed. Total RNA was isolated using the RNeasy kit from QIAGEN (Valencia, Calif.). The first strand cDNA was synthesized in a 20 µl reaction from 5 µg total RNA by reverse transcription with the SuperScriptII™ Reverse Transcriptase Kit (Life Technologies Inc., Coralville Iowa) and 100 ng random hexamers, as previously described (Zimmermann, U., Fluehmann, B., Born, W., Fischer, J. A. & Muff, R. (1997) Coexistence of Novel Amylin-Binding Sites With Calcitonin Receptors in Human Breast Carcinoma Mcf-7 Cells, Journal of Endocrinology. 155, 423–431). Subsequently the cDNA was diluted to 500 µl. In a 50 µl reaction, 10 µl cDNA was amplified in the 7700 Sequence Detector (PE Biosystems, Foster City, Calif.), using the Universal Master Mix (PE Biosystems, Foster City, Calif.) and the following PCR-primers and TaqMan™-probes at the concentrations of 300 nM and 100 nM, respectively, and PCR-primers and TaqMan™-probes for the reference gene β-actin at concentration of 50 nM. The sequences of PCR-primers and TaqMan™-probes are shown in Table 1.

TABLE 1

Sequence of PCR-primers and TaqMan ™-probes used in the amplification of cDNA of GLUT-1 (G-1), GLUT-2 (G-2), glucokinase (glu), PEPCK (PEP), ApoA1 (ApA1), ApoE (ApE), Cyp7a (C7a), Cyp4a1 (C4a1), HMG-CoA reductase (HMG), LCAT, LDLR, LFABP (LFA), LPL, TNFα, and β-actin (act)

| | | |
|---|---|---|
| G-1/p1: | GGTTCATCATCAGCATGGAGTTC | (SEQ ID NO: 1) |
| G-1/p2: | GGGCATGATTGGTTCCTTCTC | (SEQ ID NO: 2) |
| G-1/taq: | FAM-CCTGCCAAAGCGATTAACAAAGAGGCC-Tamra | (SEQ ID NO: 3) |
| G-2/p1: | CGCCCTCTGCTTCCAGTACA | (SEQ ID NO: 4) |
| G-2/p2: | AGGACCACCCCAGCAAAAA | (SEQ ID NO: 5) |
| G-2/taq: | FAM-CGGACTTCCTCGGGCCTTACGTGT-Tamra | (SEQ ID NO: 6) |
| glu/p1: | CGTGGATGGCTCCGTGTAC | (SEQ ID NO: 7) |
| glu/p2: | TGTCAGCCTGCGCACACT | (SEQ ID NO: 8) |
| glu/taq: | FAM-AGCTGCACCCGAGCTTCAAGGAGC-Tamra | (SEQ ID NO: 9) |
| PEP/p1: | CGCTGGATGTCAGAAGAGGAC | (SEQ ID NO: 10) |
| PEP/p2: | ACATGGTGCGGCCTTTCAT | (SEQ ID NO: 11) |
| PEP/taq: | FAM-AAAGCATTCAACGCCAGGTTCCCG-Tamra | (SEQ ID NO: 12) |
| ApA1/p1: | GCCACTGTGTATGTGGATGCA | (SEQ ID NO: 13) |
| ApA1/p2: | TTGCCCAAAGTGGAGGATTC | (SEQ ID NO: 14) |
| ApA1/taq: | FAM-ACAGCGGCAGAGACTATGTGTCCCAGTTT-Tamra | (SEQ ID NO: 15) |
| ApE/p1: | GGTCCAGGAAGAGCTGCAGA | (SEQ ID NO: 16) |
| ApE/p2: | CCGTCATAGTGTCCTCCATCAG | (SEQ ID NO: 17) |
| ApE/taq: | FAM-CTCCCAAGTCACACAGGAACTGACGGT-Tamra | (SEQ ID NO: 18) |
| C7a/p1: | GACTGGAAAAAATTTCATTACACTACTTCT | (SEQ ID NO: 19) |

TABLE 1-continued

Sequence of PCR-primers and TaqMan ™-probes used in the amplification
of cDNA of GLUT-1 (G-1), GLUT-2 (G-2), glucokinase (glu), PEPCK (PEP),
ApoA1 (ApA1), ApoE (ApE), Cyp7a (C7a), Cyp4a1 (C4a1), HMG-CoA
reductase (HMG), LCAT, LDLR, LFABP (LFA), LPL, TNFα, and β-actin
(act)

| | | |
|---|---|---|
| C7a/p2: | CGTGGTATTTCCATCATTTGGG | (SEQ ID NO: 20) |
| C7a/taq: | FAM-CGAAGGCATTTGGACACAGAAGCATTG-Tamra | (SEQ ID NO: 21) |
| C4a1/p1: | GCAGTTCCCATCACCTCCCT | (SEQ ID NO: 22) |
| C4a1/p2: | TGCTGTAGTTCTTTGTCACCTTGAA | (SEQ ID NO: 23) |
| C4a1/taq: | FAM-CCACTGGTTCTTTGGGCACAAGCA-Tamra | (SEQ ID NO: 24) |
| HMG/p1: | TGGCTGGTGAGTTGTCCTTG | (SEQ ID NO: 25) |
| HMG/p2: | TTATCTTTGATCTGTTGTGAACCATG | (SEQ ID NO: 26) |
| HMG/taq: | FAM-ATGTCCTGCTGCCAATGCTGCCA-Tamra | (SEQ ID NO: 27) |
| LCAT/p1: | CATGCGGATCCTGGCCT | (SEQ ID NO: 28) |
| LCAT/p2: | TCTCTCAGCTTTATGTTGGACATGA | (SEQ ID NO: 29) |
| LCAT/taq: | FAM-AGGTGACAACCAGGGCATCCCG-Tamra | (SEQ ID NO: 30) |
| LDLR/p1: | GGTGGTCAGCAGCCCT | (SEQ ID NO: 31) |
| LDLR/p2: | CAGCTGCGATGGATACACTCA | (SEQ ID NO: 32) |
| LDLR/taq: | FAM-CCTCCCTCGAGTTCCACTGTGGCAGTA-Tamra | (SEQ ID NO: 33) |
| LFA/p1: | CAAGGTGATCCACAATGAGTTCA | (SEQ ID NO: 34) |
| LFA/p2: | GACCTTTTCCCCAGTCATGGT | (SEQ ID NO: 35) |
| LFA/taq: | FAM-TGGGGGAGGAGTGCGAACTGGAGA-Tamra | (SEQ ID NO: 36) |
| LPL/p1: | TCGGGCCCAGCAACTT | (SEQ ID NO: 37) |
| LPL/p2: | GGCCACATCATTTCCCACC | (SEQ ID NO: 38) |
| LPL/taq: | FAM-TCCAGTGTCTGCCGGCTATACCAAGC-Tamra | (SEQ ID NO: 39) |
| TNFα/p1: | TCGTAGGTCAAACCACCAAGC | (SEQ ID NO: 40) |
| TNFα/p2: | TATTGGCCAGGAGGGCGT | (SEQ ID NO: 41) |
| TNFα/taq: | FAM-AGGAGCAGCTGGAGTGGCTGAGCCAG-Tamra | (SEQ ID NO: 42) |
| act/p1: | GACAGGATGCAGAGGAGATTACTG | (SEQ ID NO: 43) |
| act/p2: | CCACCGATCCACACAGAGTACTT | (SEQ ID NO: 44) |
| act/taq: | VIC-TCAAGATCATTGCTCCTCCTGAGCGC-Tamra | (SEQ ID NO: 45) |

Figure 4:
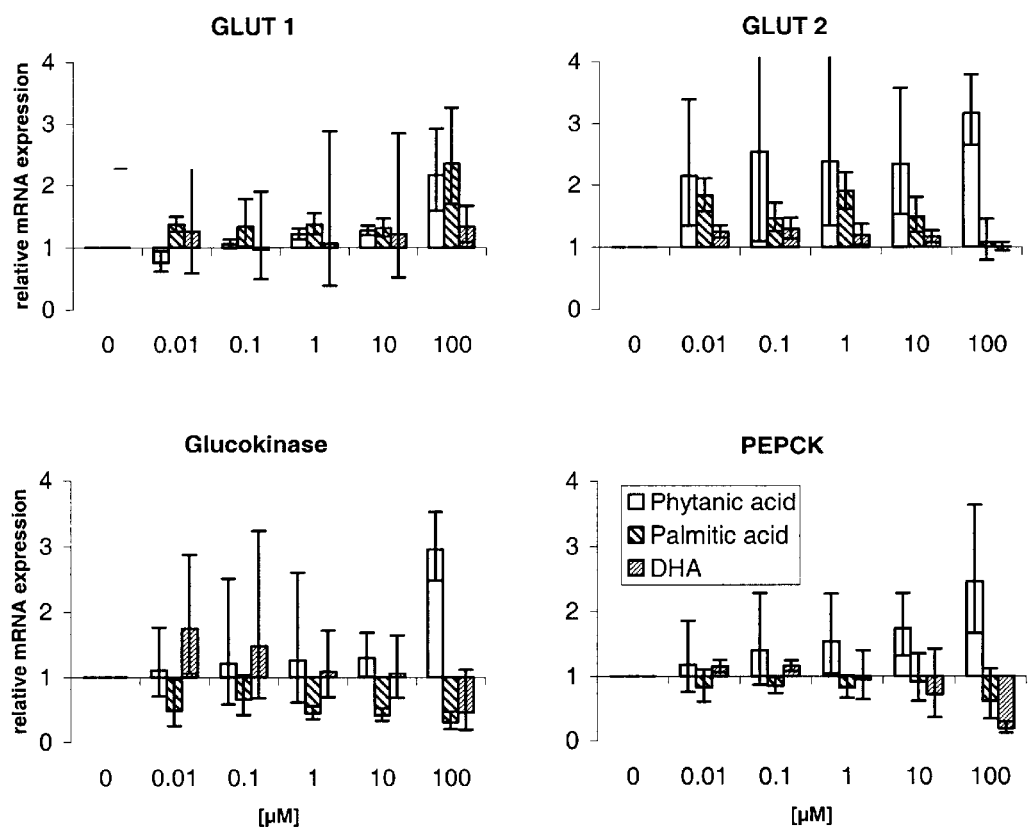
FIG. 4 shows mRNA levels for GLUT-1, GLUT-2, glucokinase and PEPCK were determined with the TaqMan™ methodology after a 24 h stimulation of the rat primary hepatocytes with 100 µM phytanic acid, palmitic acid and DHA. mRNA levels were normalized to β-actin expression and expressed relative to untreated cells. The data is presented as means of 3 independent experiments. Error bars were calculated as described in Example 3.

The induction of gene expression, and corresponding error bars were calculated from 3 independent experiments using the ΔCT method according to the manufacturer's protocol.

mRNA levels of the reference genes encoding for β-actin, glyceraldehyde 3-phosphate dehydrogenase (GAPDH), hypoxanthine ribosyl transferase (HPRT), and 18S ribosomal RNA were compared in cells treated for 24 h with or without 100 µM phytanic acid. mRNA levels of β-actin and 18S ribosomal RNA were not affected by phytanic acid (not shown). Therefore, all results were normalized to β-actin mRNA levels. Measurement of mRNA levels for GLUT1 and PEPCK in response to 100 µM phytanic acid revealed after 6 hours a maximal 5.6 (5.1–6.2)-fold and 4.4 (3.4–5.7)-fold induction, respectively (FIG. 3). mRNA levels of GLUT-2 and glucokinase were found to be maximal after a 24h stimulation period with phytanic acid. A 2.2 (1.6–2.9)-fold and 2.4 (1.7–3.3)-fold induction of mRNA levels for GLUT1 was observed in hepatocytes stimulated for 24 h with 100 µM phytanic acid and palmitic acid, respectively (FIG. 4). Lower phytanic acid and palmitic acid concentrations as well as DHA concentrations up to 100 µM did not affect GLUT1 mRNA levels.

Figure 5:
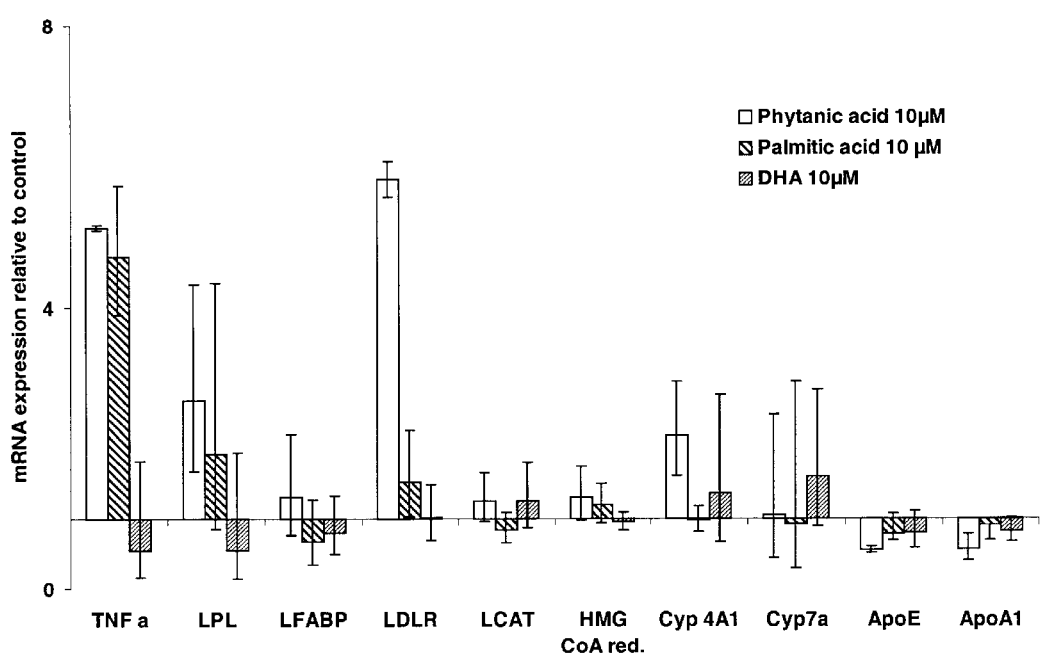
FIG. 5 shows mRNA levels for ApoA1, ApoE, Cyp7a, Cyp4a1, HMG-CoA reductase LCAT, LDLR, LFABP, LPL, and TNFα. The mRNA levels were determined with the TaqMan™ methodology after a 24 h stimulation of the rat primary hepatocytes with 10 µM phytanic acid, palmitic acid, and DHA. mRNA levels were normalized to β-actin expression and expressed relative to untreated cells. The data is presented as means of 3 independent experiments. Error bars were calculated as described in Example 3.

Treatment of the cells for 24 h with phytanic acid (0.01–100 µM) induced mRNA levels for GLUT-2 at least 2-fold, with a maximal induction of 3.2 (2.7–3.8)-fold (100 µM) (FIG. 4). However, at low palmitic acid concentrations a minor induction of GLUT-2 mRNA levels was observed. In comparison, DHA did not affect GLUT-2 mRNA levels. mRNA levels of glucokinase and PEPCK were induced by 100 µM phytanic acid 3.0 (2.5–3.4)-fold and 2.5 (1.7–3.6)-fold. The transcription of glucokinase as well as PEPCK mRNA was reduced by 100 µM palmitic acid and DHA. After phytanic acid treatment (10 µM for 24 h) we observed an increase for the transcripts of cytochrome P450/4A1 (Cyp4a1), 3-hydroxy 3-methylglutaryl-CoA (HMG-CoA)-reductase, lipoprotein lipase (LPL), low-density lipoprotein receptor (LDLR), PEPCK, and tumor necrosis factor a (TNFα). In contrast, the mRNAs encoding for apolipoprotein A1 (ApoA1) and apolipoprotein E (ApoE) were down-regulated by phytanic acid. mRNA levels for liver fatty acid binding protein (LFABP), cholesterol 7α-hydroxylase and glucokinase (Cyp7a) remained unaffected (FIG. 5).

Example 4

In vivo Study on the Efficacy of Phytanic Acid

Figure 7:
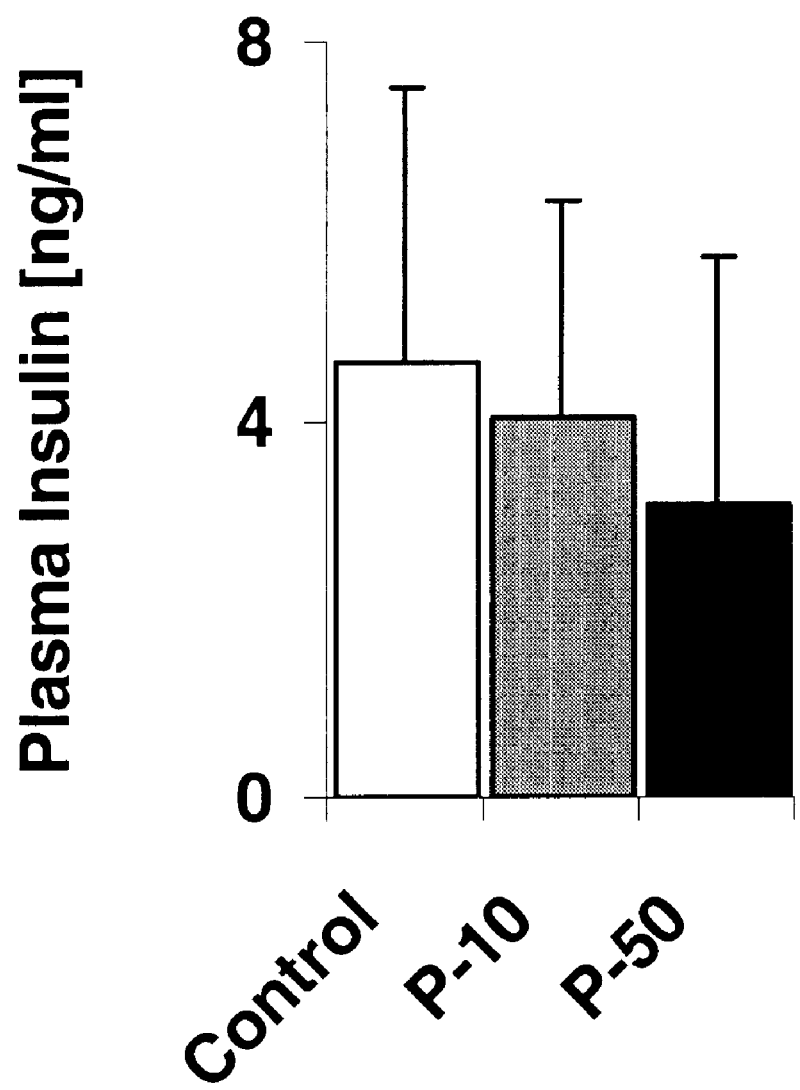
FIG. 7 shows plasma insulin concentrations after the administration of 150 mg phytanic acid/kg feed (P-10, shaded bars) and 750 mg phytanic acid/kg feed (P-50, closed bars), respectively or control chow (control, open bars). Male Wistar rats were adapted for two days and then fed with the respective substance. The values are means±SD (see Example 4).

To determine the beneficial effect of phytanic acid on plasma insulin levels, a study was performed using male Wistar rats. The animals were adapted for two days and then fed with control chow, 150 mg phytanic acid/kg feed (P-10), and 750 mg phytanic acid/kg feed (P-50), respectively. Blood samples were taken at day 7 and the insulin concentration in the plasma was measured (FIG. 7). The application of different concentrations of phytanic acid could reduce the plasma insulin.

The invention being thus described, it will be obvious that the same may be varied in many ways. Such variations are not to be regarded as a departure from the spirit and scope of the invention and all such modifications are intended to be included within the scope of the following claims.

What is claimed is:

1. A composition for the treatment of non-insulin dependent diabetes mellitus comprising from about 0.1 to about 1000 mg of phytanic acid or a derivative thereof and a pharmaceutically acceptable carrier.

2. A composition according to claim 1 wherein the pharmaceutically acceptable carrier is selected from the group consisting of diluent, filler, disintegrate, wetting agent, lubricant, colorant, flavorant, adjuvants, and combinations thereof.

3. A composition according to claim 2 wherein the carrier is selected from the group consisting of microcrystalline cellulose, starch, sodium starch glycollate, polyvinylpyrrolidone, polyvinylpolypyrrolidone, magnesium stearate, sodium lauryl sulfate, sucrose, and combinations thereof.

4. A composition according to claim 1 comprising from about 0.1 to about 500 mg of phytanic acid or a derivative thereof.

5. A composition according to claim 4 comprising from about 0.1 to about 100 mg of phytanic acid or a derivative thereof.

6. A dietary supplement comprising a composition for the treatment of non-insulin dependent diabetes mellitus comprising from about 0.1 to about 1000 mg of phytanic acid or a derivative thereof and an additive or adjuvant.

* * * * *